(12) United States Patent
Müller et al.

(10) Patent No.: US 6,891,278 B2
(45) Date of Patent: May 10, 2005

(54) SEMICONDUCTOR COMPONENT

(75) Inventors: Gustav Müller, Osterhofen (DE); Axel Schubert, München (DE); Karl-Heinz Schlereth, Burglengenfeld (DE); Harald Böttner, Freiburg (DE)

(73) Assignee: Infineon Technologies AG, Munich (DE)

( * ) Notice: Subject to any disclaimer, the term of this patent is extended or adjusted under 35 U.S.C. 154(b) by 0 days.

(21) Appl. No.: 10/644,118

(22) Filed: Aug. 20, 2003

(65) Prior Publication Data

US 2004/0046223 A1 Mar. 11, 2004

(30) Foreign Application Priority Data

Aug. 20, 2002 (DE) .......................................... 102 38 843

(51) Int. Cl.[7] .......................... H01L 23/38; H01L 27/16; H01L 35/00; H01L 35/28
(52) U.S. Cl. ........................................ 257/930; 257/706
(58) Field of Search ................................ 257/930, 706, 257/707

(56) References Cited

U.S. PATENT DOCUMENTS 6,219,364 B1 * 4/2001 Dei ............................. 372/36
6,512,291 B2 * 1/2003 Dautartas et al. ........... 257/706

FOREIGN PATENT DOCUMENTS

| DE | 4229500 A1 | 3/1994 |
| DE | 19845104 A1 | 4/2000 |
| DE | 10004390 C2 | 5/2002 |
| JP | 2001320003 | 11/2001 |
| WO | 00/19548 | 4/2000 |

OTHER PUBLICATIONS

Japanese Patent Abstract No. 04012558 A (Shintaro et al.), dated Jan. 17, 1992.
Japanese Patent Abstract No. 2002050727 A (Fumiyoshi et al.), dated Feb. 15, 2002.
Japanese Patent Abstract No. 01245549 A (Hiroshi), dated Sep. 29, 1989.

* cited by examiner

*Primary Examiner*—Phat X. Cao
(74) *Attorney, Agent, or Firm*—Laurence A. Greenberg; Werner H. Stemer; Gregory L. Mayback

(57) ABSTRACT

A semiconductor component has at least one Peltier element and at least one thermogenerator element that are thermally coupled to one another via a coupling device. By virtue of the thermal coupling of the Peltier element and the thermogenerator element through the coupling device, it is possible to use the Peltier element to cool a microstructure, in particular an optoelectronic component (e.g. a laser diode). Efficient temperature regulation and efficient operation of an optoelectronic component are thus possible.

19 Claims, 6 Drawing Sheets

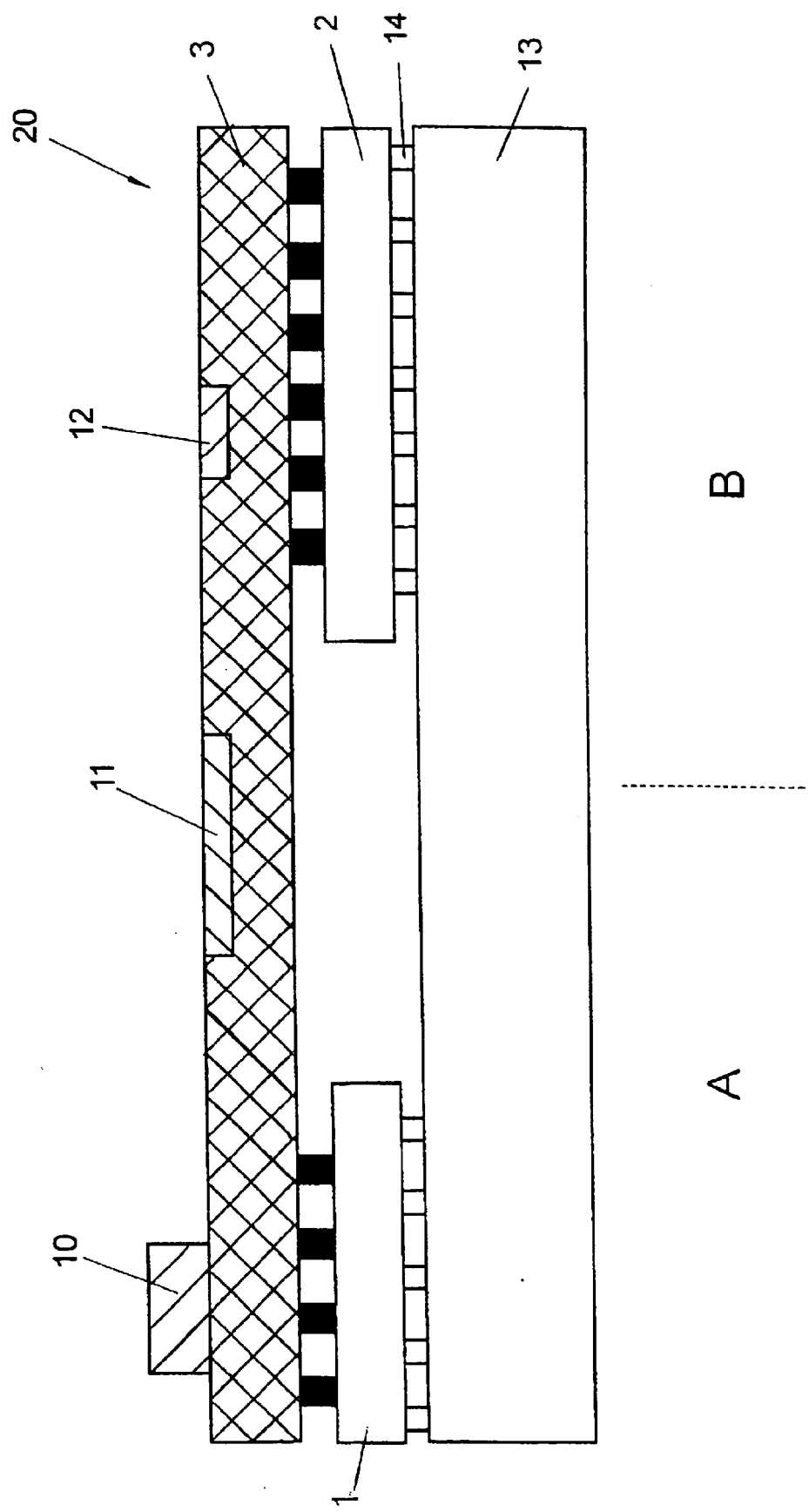

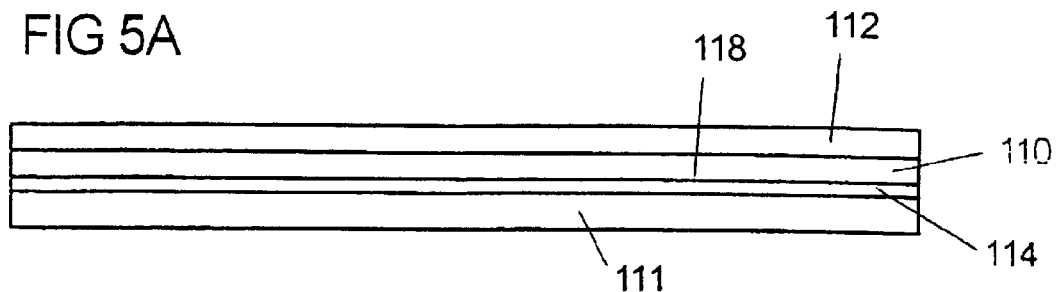
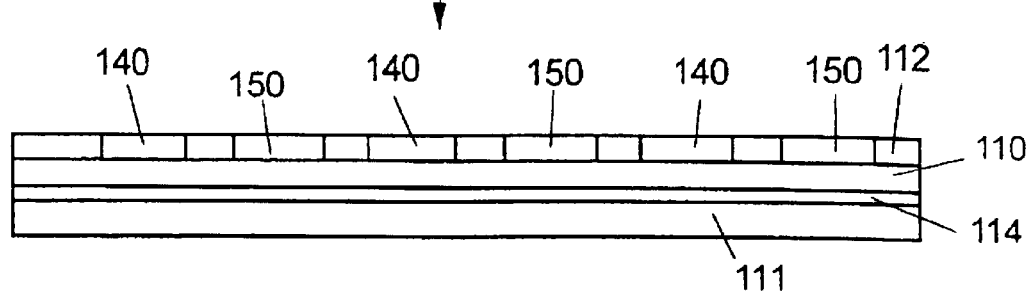
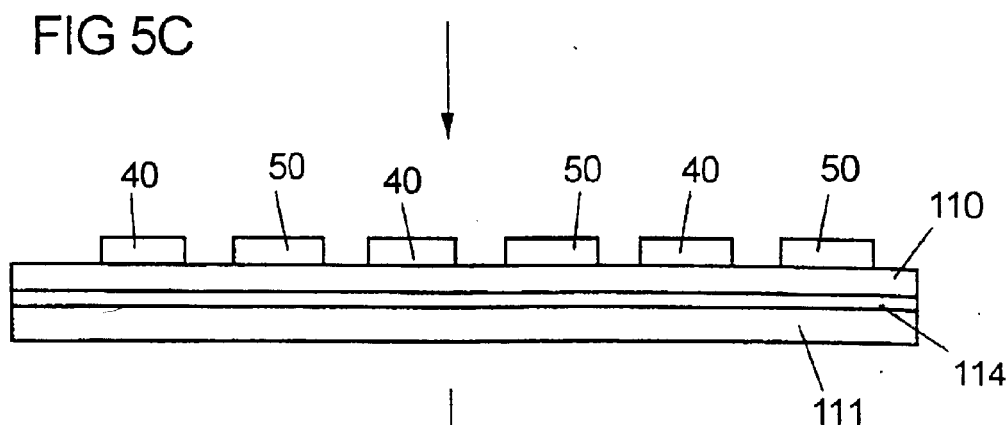
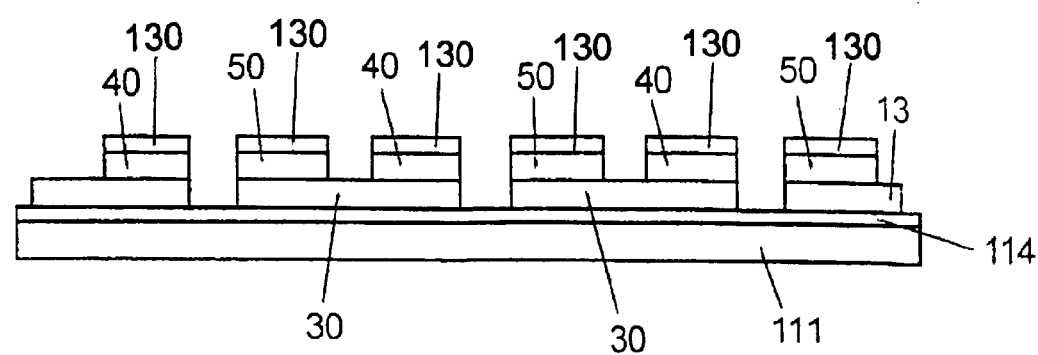

SEMICONDUCTOR COMPONENT

BACKGROUND OF THE INVENTION

Field of the Invention

The invention relates to a semiconductor component having at least one microstructure being an optoelectronic component.

Optoelectronic communications technology nowadays makes use of microstructures, such as e.g. laser diodes, which have a considerable cooling requirement and require an integrated circuit as a controller device. Other active or passive electronic components or else microstructures from the field of biotechnology (e.g. biochips) also frequently need to be cooled.

Such microstructures can be cooled by convection or thermal conduction. In the case of convective cooling, a gas stream is brought into contact with the microstructure to be cooled. In the case of cooling by thermal conduction, a heat sink is connected to the microstructure to be cooled. Such a heat sink may contain e.g. a Peltier element known per se.

Published, Non-Prosecuted German Patent Application DE 198 45 104 A discloses a thermoelectric transducer produced in a sandwich configuration. The transducer has a series of thermoelement cells, which are connected in series by a common interconnect. Such a transducer can also be used as a heat sink for optoelectronic components.

In optoelectronics and in other fields, the microstructures are becoming smaller, so that a higher integration density, in particular also for cooling elements and controller devices, is desirable.

SUMMARY OF THE INVENTION

It is accordingly an object of the invention to provide a semiconductor component that overcomes the above-mentioned disadvantages of the prior art devices of this general type, with which temperature regulation and also an operation of a microstructure, in particular of an optoelectronic component, are possible in an efficient manner.

With the foregoing and other objects in view there is provided, in accordance with the invention, a semiconductor component. The semiconductor component contains at least one microstructure, at least one Peltier element for cooling the microstructure, at least one thermogenerator element, and a coupling device thermally coupling the Peltier element and the thermogenerator element to one another. The coupling device additionally supports the microstructure.

By virtue of the thermal coupling of the Peltier element and the thermogenerator element via the coupling device, it is possible by use of the Peltier element to cool a microstructure, in particular an optoelectronic component (e.g. a laser diode), but at the same time to use a temperature difference that arises by the thermogenerator element for voltage generation purposes. It is thus possible to achieve, in particular, a compact configuration of the entire component with a temperature regulating device.

In an advantageous manner, the coupling device has a semiconductor layer, in particular a silicon semiconductor layer, or contains silicon. Silicon has a high thermal conductivity, silicon also being suitable, in particular, for the construction of semiconductor structures.

In an advantageous manner, the Peltier element and/or the thermogenerator element are constructed as a thermoelectric transducer in a sandwich configuration. Such a transducer is disclosed e.g. in DE 198 45 104 A1 and will also be described later. In this case, it is particularly advantageous if the thermoelectric transducer in a sandwich configuration has a plurality of series-connected thermoelement cells, which are connected to one another in series by a plurality of electrical interconnects. Each thermoelement cell has a first body made of a first thermoelectric material of a first conductivity type and a second body made of a second thermoelectric material of a second conductivity type, which are connected to one another by a second electrical interconnect and which are disposed in a sandwich-like manner between a first substrate wafer and a second electrically insulating substrate wafer. Alternatively, a second substrate wafer has an insulating layer, the first substrate wafer and the second substrate wafer are connected to one another in such a way that the first and second interconnects and the first and second bodies are disposed between the two substrate wafers and form a plurality of series-connected thermoelement cells. A transducer can be realized as a semiconductor sandwich construction, which permits particularly miniaturized structural forms. Such a sandwich structure can be produced in a simple manner by photomask and etching techniques.

The semiconductor component according to the invention can advantageously be used in conjunction with a laser component coupled to the coupling device, in particular a laser diode or a laser-based gas sensor.

Furthermore, it is advantageous if provision is made for at least one integrated circuit and/or a thermistor for controlling at least one laser diode.

In this case, it is advantageous if the laser diode, the integrated circuit and/or the thermistor are coupled to the coupling device in a hybrid design.

It is also advantageous if the laser diode, the integrated circuit and/or the thermistor are coupled to the coupling device in a monolithic integrated design.

The energy requirement of the optoelectronic components is lowered if at least one thermogenerator element is part of the voltage supply for an integrated circuit.

In an advantageous manner, at least one microstructure is formed as an active electronic component, a passive electronic component, as a microreactor, or as a cavity for receiving a liquid, in particular in the context of a DNA analysis and/or DNA synthesis. The microstructures also need temperature control during operation, and this can be achieved in an efficient manner by the semiconductor component according to the invention.

It is also advantageous if a microstructure whose temperature is to be regulated has a receptacle device for the cultivation of cells, in particular yeasts, human cells or bacteria.

In a further advantageous refinement, at least one microstructure whose temperature is to be regulated is formed as a gas chromatograph capillary disposed in the coupling device.

In an advantageous manner, the semiconductor component according to the invention has a device for smoothing the current generated by the thermogenerator element. It is particularly advantageous, since it saves space, if the device for smoothing the current is disposed in an integrated circuit of the semiconductor component.

It is also advantageous if at least one thermogenerator element can be used as a measurement sensor for temperature regulation.

Other features which are considered as characteristic for the invention are set forth in the appended claims.

Although the invention is illustrated and described herein as embodied in a semiconductor component, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 3 is a diagrammatic, side-elevational view of a second embodiment of the semiconductor component according to the invention with a monolithic integrated configuration of the laser diode, the integrated circuit and the thermistor;

FIGS. 5A–5G are diagrammatic, sectional views showing an illustration of the production of the semiconductor component in a sandwich configuration.

DESCRIPTION OF THE PREFERRED EMBODIMENTS

Figure 1:
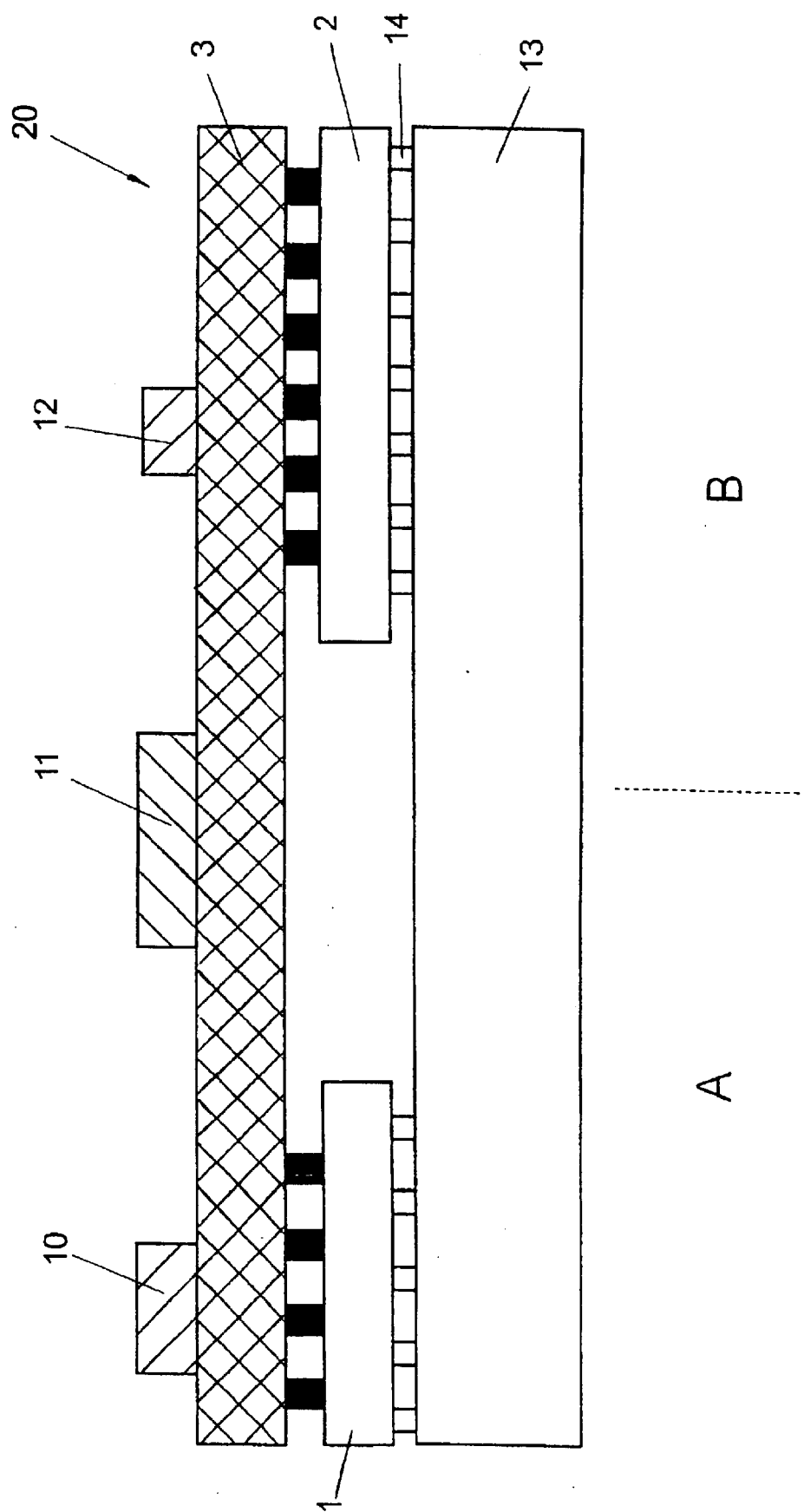
FIG. 1 is a diagrammatic, side-elevational view of a first embodiment of a semiconductor component according to the invention with a hybrid configuration of a laser diode, an integrated circuit, and a thermistor.
Figure 5E:
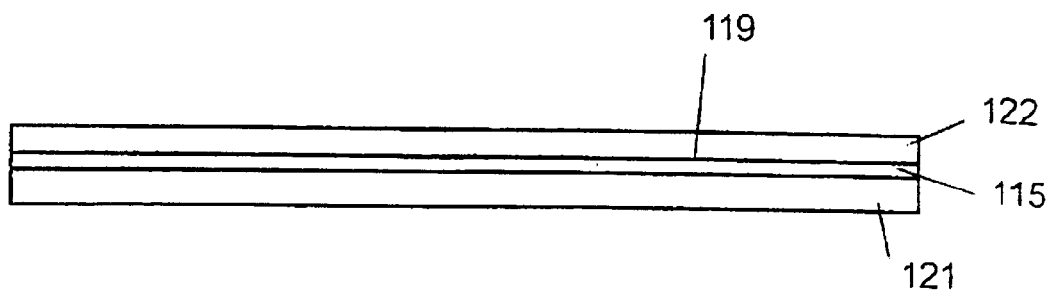

Referring now to the figures of the drawing in detail and first, particularly, to FIG. 1 thereof, there is shown a first embodiment of a semiconductor component 20 according to the invention. The semiconductor component 20 has a coupling device 3, by which a Peltier element 1 and a thermogenerator element 2 are thermally coupled to one another. In this case, the coupling device 3 is formed as a highly doped silicon layer that serves as a thermal short circuit on account of high thermal conductivity. In this case, the Peltier element 1 and thermogenerator element 2 are formed as a sandwich component whose production is disclosed in Published, Non-Prosecuted German Patent Application DE 198 45 104 A1. The production, according to the invention, will be described in more detail in connection with FIG. 5.

On the semiconductor component 20 there is disposed, as an optoelectronic component, a laser diode 10 in a hybrid design. In this case, the Peltier element 1 is disposed below the laser diode 10 and serves for cooling the laser diode 10. Therefore, the left-hand side A of the semiconductor component 20 is also called the Peltier side.

In this case, the laser diode 10 is used as a microstructure 10. In principle, however, it is also possible to dispose other microstructures, such as e.g. filters, gratings or else sensors on the coupling device 3 in order to regulate temperature by use of the semiconductor component 20 according to the invention. The microstructure may also be a depression that forms a microreactor. Microstructures whose temperature are to be regulated and which can be found in the field of biotechnology can also be disposed on the coupling device 3.

On the right-hand side B of the semiconductor component 20, the thermogenerator side, the thermogenerator element 2 serves for converting a temperature difference into a voltage. The temperature difference exists between the relatively hot laser diode 10 and the ambient temperature in this case. The voltage generated by the thermogenerator 2 can then be used to supply an integrated circuit 11, which is disposed on the coupling device 3 for the purpose of driving the laser diode 10. In the present exemplary embodiment, the integrated circuit 11 is disposed in a hybrid design on the coupling device 3.

A thermistor 12 (NTC resistor) is used as measurement pickup for the integrated circuit 11, the thermistor 12 in this case likewise being connected to the coupling device 3 in a hybrid design.

The semiconductor component 20 according to the invention thus has a compact combination of hitherto separate functional groups (Peltier cooler, thermogenerator). The thermogenerator 2 may serve for relieving the load on a non-illustrated external voltage source for the integrated circuit 11. The thermogenerator 2 is integrated with the Peltier element 1—required for cooling the laser diode 10—in a component.

A circuit 21 required for smoothing the voltage of the thermogenerator 2 is disposed in the integrated circuit 11.

The semiconductor component 20 on the Peltier side A and the thermogenerator side B is connected to a heat sink 13 via gold contacts 14 (gold bumps).

The laser diode 10 was used as the component to be cooled in the present example. In principle, the semiconductor component 20 according to the invention can also be used for cooling other optoelectronic components, such as, e.g. a laser-based gas sensor.

Figure 2:
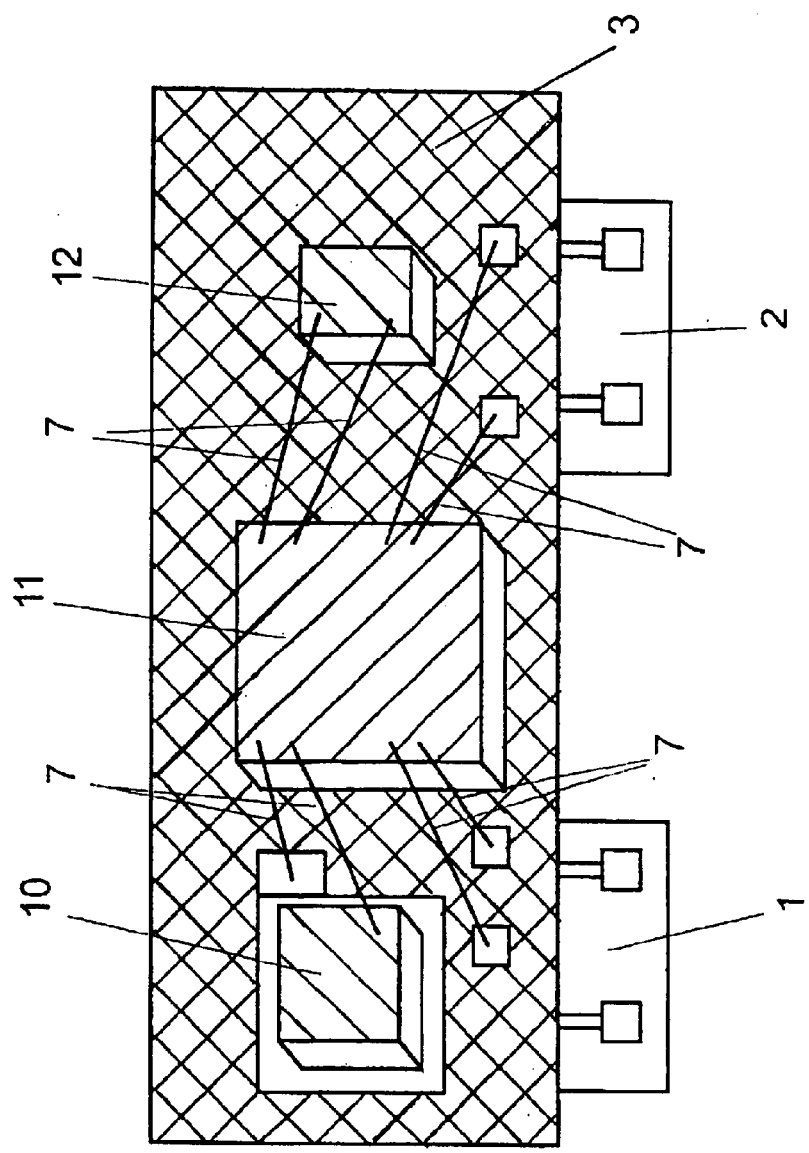
FIG. 2 is a perspective illustration of the first embodiment according to FIG. 1.

FIG. 2 diagrammatically represents the first embodiment of the semiconductor component 20 according to the invention in a perspective view.

In this case, the upper plane is formed by the silicon layer of the coupling device 3; situated underneath is the lower plane of the Peltier element 1 and of the thermogenerator element 2.

The laser diode 10, the integrated circuit 11 and the thermistor 12 are disposed in a hybrid design on the coupling device 3.

The integrated circuit 11 is connected to the Peltier element 1, the thermogenerator element 2, the thermistor 12 and the laser diode 10 via lines 7.

Figure 2A:
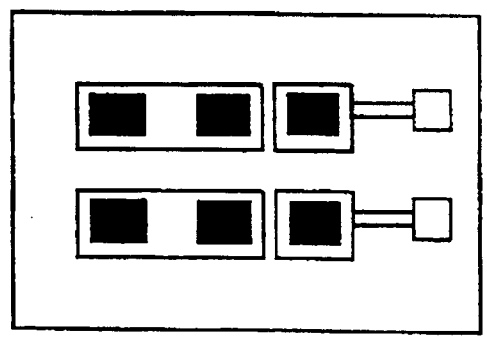
FIG. 2a is a plan view of a detail of the Peltier element of the first embodiment according to FIG. 1.

FIG. 2A shows a plan view of the Peltier element 1.

FIG. 3 illustrates a second embodiment of the semiconductor component 20 according to the invention. The basic construction corresponds to the first embodiment, and so reference may be made to the corresponding description of FIG. 1.

In contrast to the first embodiment, in this case, the integrated circuit 11 and the thermistor 12 are incorporated as layer structures into the silicon of the coupling device 3. Monolithic integration of the integrated circuit 11 and of the thermistor 12 is thus afforded.

In an alternative that is not illustrated here, the component 10 to be cooled may also be monolithically integrated into the coupling device 3.

Figure 4:
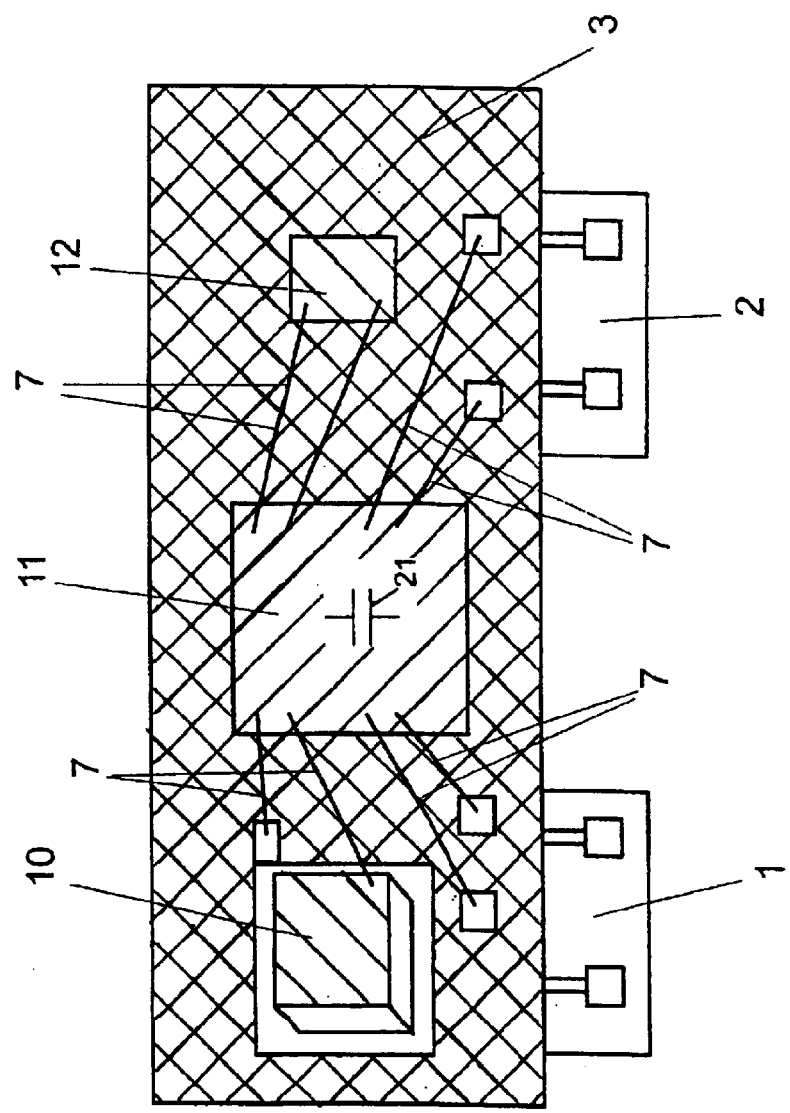
FIG. 4 is a perspective illustration of the second embodiment according to FIG. 3.

FIG. 4, analogously to FIG. 2, illustrates a perspective view of the second embodiment of the semiconductor component 20 according to the invention. It can be seen in this case that the integrated circuit 11 and the thermistor 12 are integrated into the upper plane of the coupling device 3.

Figure 4A:
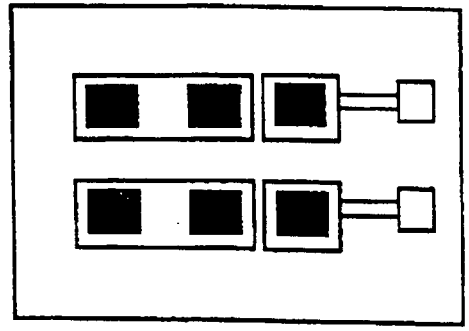
FIG. 4a is a plan view of a detail illustration of the Peltier element of the second embodiment according to FIG. 3.

FIG. 4A shows once again a plan view of the peltier element 1.

FIGS. 5A to 5G describe the production of a component in the form of a sandwich configuration. The sandwich component can then be used in a semiconductor component according to the invention as the Peltier element 1 and/or the thermogenerator element 2. Other production methods for a thermoelectric transducer can be gathered from DE 198 45 104 A1 which is hereby incorporated herein.

A first electrically conductive layer 110 is produced on a main area 118 of a first substrate wafer 111. The layer 110 contains e.g. a metal layer, a metal layer sequence or a highly doped and hence highly conductive semiconductor layer (e.g. diffused silicon).

The first substrate wafer 111 has a low electrical conductivity overall and contains, for example, semi-insulating silicon or has an electrically insulating layer 114 (e.g. a silicon oxide or silicon nitride layer) on the side of the main area 118.

A layer 112 made of thermoelectric material (e.g. $Bi_2Te_3$, $Bi_2Se_3$, PbTe, Si, Ge, etc.) is deposited on the first electrically conductive layer 110 (see FIG. 5A). A plurality of doped regions 140 of a first conductivity type (e.g. p-conducting) and a plurality of doped regions 150 of a second conductivity type (e.g. n-conducting) are subsequently formed in the layer 112 by use of photomask technology and diffusion (see FIG. 5B).

The layer 112 with the doped regions 140, 150 is then patterned by using one or more photomask and performing etching processes known per se to form first bodies 40 and second bodies 50 (see FIG. 5C).

The first electrically conductive layer 110 is then likewise patterned by use of a photomask and etching processes in such a way as to produce on the first substrate wafer 111 a plurality of mutually separate thermoelement cells (FIG. 5C) which each have a first body 40 and a second body 50 and a first electrical interconnect 30 connecting them (FIG. 5D).

A metallization layer 130 (e.g. made of gold) is disposed on the sides of the first and second bodies 40, 50 opposite to the first interconnect 30.

Figure 5F:
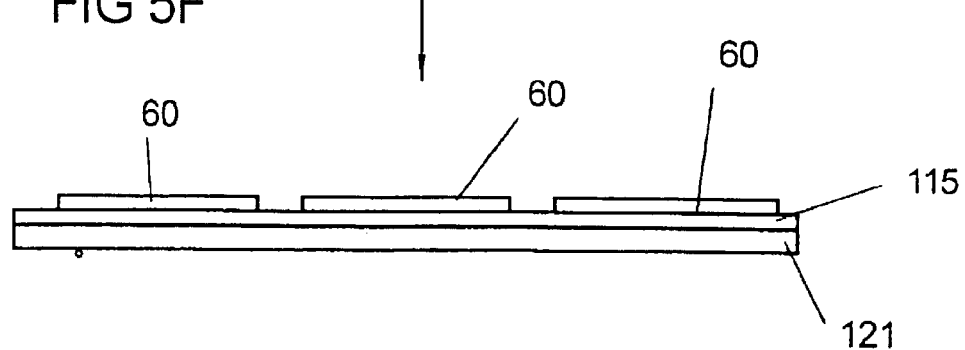

A second electrically conductive layer 122 is disposed on a main area 119 of a second substrate wafer 121 (FIG. 5E) and patterned to form second electrical interconnects 60 (FIG. 5F).

Analogously to the first substrate wafer 111, the second substrate wafer 121 has a low electrical conductivity overall and contains, for example, semi-insulating silicon. The second substrate wafer 121 may also have an electrically insulating layer 115 (e.g. a silicon oxide or silicon nitride layer) on the side of the main area 119.

Figure 5G:
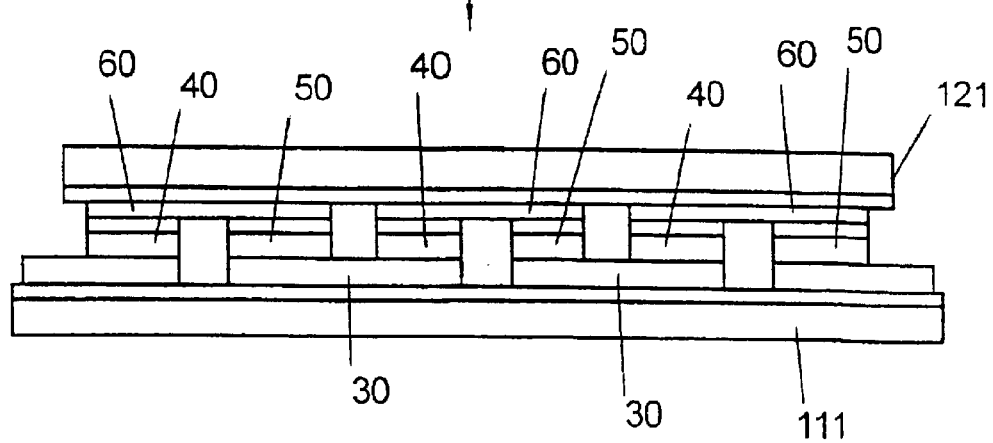

After the patterning of the second interconnects 60, the second substrate wafer 121 is placed with the latter onto the metallization layers 130 of the first and second bodies 40, 50 and aligned in such a way that the second interconnects 60 bear on the metallization layers 130 of the first and second bodies 40, 50 and the previously formed pairs each containing a first and a second body 40, 50 are connected up to one another in series (FIG. 5G).

The second electrical interconnects 60 and the metallization layers 130 are then connected to one another, e.g. by soldering, adhesive bonding or thermocompression.

This results in a sandwich composite containing the two substrate wafers 111, 121 and the thermoelement cells situated in between.

The embodiment of the invention is not restricted to the preferred exemplary embodiments specified above. Rather, a number of variants are conceivable which make use of the semiconductor component according to the invention in the case of embodiments of fundamentally different configuration too.

We claim:

1. A semiconductor component, comprising:
    at least one microstructure;
    at least one Peltier element for cooling said microstructure;
    at least one thermogenerator element; and
    a coupling device thermally coupling said Peltier element and said thermogenerator element to one another, said coupling device supporting said microstructure.

2. The semiconductor component according to claim 1, wherein said coupling device has a highly doped semiconductor layer.

3. The semiconductor component according to claim 1, wherein at least one of said Peltier element and said thermogenerator element are constructed as a thermoelectric transducer in a sandwich configuration.

4. The semiconductor component according to claim 3,
    further comprising a plurality of first electrical interconnects and a plurality of second electrical interconnects;
    further comprising a first substrate wafer;
    further comprising a second electrically insulating substrate wafer; and
    wherein said thermoelectric transducer has a plurality of series-connected thermoelement cells connected to one another in series by said first electrical interconnects, each of said thermoelement cells having a first body made of a first thermoelectric material of a first conductivity type and a second body made of a second thermoelectric material of a second conductivity type and connected to one another by one of said second electrical interconnects, said thermoelement cells disposed in a sandwich-like manner between said first substrate wafer and said second electrically insulating substrate wafer.

5. The semiconductor component according to claim 1, wherein said microstructure includes at least one laser component coupled to said coupling device.

6. The semiconductor component according to claim 5, further comprising a least one component selected from the group consisting of an integrated circuit and a thermistor for controlling said laser component being a laser diode supported by said coupling device.

7. The semiconductor component according to claim 6, wherein at least one of said laser diode, said integrated circuit and said thermistor are coupled to the coupling device in a hybrid design.

8. The semiconductor component according to claim 1, wherein said microstructure has a laser diode, and at least one of said laser diode, said integrated circuit, and said thermistor are coupled to said coupling device in a monolithic integrated design.

9. The semiconductor component according to claim 1, wherein said thermogenerator element is part of a voltage supply for an integrated circuit.

10. The semiconductor component according to claim 1, wherein said microstructure is selected from the group consisting of an active electronic component, a passive electronic component, a microreactor, and a cavity for receiving a liquid in a context of a DNA analysis or DNA synthesis.

11. The semiconductor component according to claim 1, wherein said microstructure whose temperature is to be regulated has a receptacle device for cultivation of cells being one of yeast cells, human cells and bacteria cells.

12. The semiconductor component according to claim 1, wherein said microstructure whose temperature is to be regulated is a gas chromatograph capillary disposed in said coupling device.

13. The semiconductor component according to claim 1, further comprising a smoothing device for smoothing a current generated by said thermogenerator element.

14. The semiconductor component according to claim 13, further comprising an integrated circuit and said smoothing device is disposed in said integrated circuit.

15. The semiconductor component according to claim 1, wherein said thermogenerator element is a measurement sensor for temperature regulation.

16. The semiconductor component according to claim 3,
further comprising a plurality of first electrical interconnects and a plurality of second electrical interconnects;
a first substrate wafer;
a second substrate wafer having an insulating layer;
wherein said thermoelectric transducer has a plurality of series-connected thermoelement cells connected to one another in series by said first electrical interconnects, each of said thermoelement cells having a first body made of a first thermoelectric material of a first conductivity type and a second body made of a second thermoelectric material of a second conductivity type and connected to one another by one of said second electrical interconnects; and
wherein said first substrate wafer and said second substrate wafer connected to one another such that said first and second electrical interconnects and said first and second bodies are disposed between said first and second substrate wafers and form said plurality of series-connected thermoelement cells.

17. The semiconductor component according to claim 5, wherein said laser component is selected from the group consisting of a laser diode and a laser-based gas sensor.

18. The semiconductor component according to claim 2, wherein said highly doped semiconductor layer is a highly doped silicon semiconductor layer.

19. The semiconductor component according to claim 5, wherein said microstructure is an optoelectronic component.

* * * * *